US008483809B2

(12) United States Patent
Kim et al.

(10) Patent No.: US 8,483,809 B2
(45) Date of Patent: Jul. 9, 2013

(54) REAL-TIME ELECTROCARDIOGRAM MONITORING SYSTEM AND METHOD, PATCH-TYPE ELECTROCARDIOGRAPH, TELECOMMUNICATION APPARATUS

(75) Inventors: Yoon Nyun Kim, Daegu-si (KR); Hee Joon Park, Gumi-si (KR); Jyung Hyun Lee, Daegu-si (KR); Hyo Chan Jeon, Daegu-si (KR)

(73) Assignee: Keimyung University Industry Academic Cooperation Foundation, Daegu-si (KR)

( * ) Notice: Subject to any disclaimer, the term of this patent is extended or adjusted under 35 U.S.C. 154(b) by 277 days.

(21) Appl. No.: 12/935,000

(22) PCT Filed: Mar. 12, 2009

(86) PCT No.: PCT/KR2009/001243
§ 371 (c)(1),
(2), (4) Date: Sep. 27, 2010

(87) PCT Pub. No.: WO2009/119984
PCT Pub. Date: Oct. 1, 2009

(65) Prior Publication Data
US 2011/0021902 A1 Jan. 27, 2011

(30) Foreign Application Priority Data

Mar. 27, 2008 (KR) .................. 10-2008-0028231

(51) Int. Cl.
*A61B 5/04* (2006.01)
(52) U.S. Cl.
USPC ............ 600/509; 600/372; 600/384; 600/386
(58) Field of Classification Search
USPC .......... 600/372, 382, 384, 386–393, 508–509
See application file for complete search history.

(56) References Cited

U.S. PATENT DOCUMENTS

| 5,307,818 | A  | * | 5/1994 | Segalowitz | 600/509 |
| 6,643,541 | B2 | * | 11/2003 | Mok et al. | 600/546 |
| 7,942,824 | B1 | * | 5/2011 | Kayyali et al. | 600/538 |
| 2004/0039254 | A1 | * | 2/2004 | Stivoric et al. | 600/300 |

* cited by examiner

FOREIGN PATENT DOCUMENTS

| KR | 10-0691513 B1 | * | 7/2006 |
| KR | 10-0693861 B1 | * | 10/2006 |
| KR | 10-0813166 B1 | * | 3/2008 |

*Primary Examiner* — Linda Dvorak
*Assistant Examiner* — Brian M Antiskay
(74) *Attorney, Agent, or Firm* — Revolution IP, PLLC

(57) ABSTRACT

The present invention relates to a real-time electrocardiogram monitoring system and method, a patch-type electrocardiograph and a telecommunication apparatus. The real-time electrocardiogram monitoring system includes: a patch-type electrocardiograph which is attached to a skin of a subject in the form of a patch, measures an electrocardiogram of the subject, and generates and transmits first electrocardiogram data of a first frame format for near-field transmission of the measured electrocardiogram signal; a relay-type communication device which receives the first electrocardiogram data from the patch-type electrocardiograph, extracts electrocardiogram data, and combines the extracted electrocardiogram with identification information of the subject to generate second electrocardiogram data of a second frame format for far-field transmission; a monitoring server which receives the second electrocardiogram data from the relay-type communication device, extracts the electrocardiogram data and the subject identification information, and classifies, stores and outputs in real time the electrocardiogram data based on the subject identification information; and a repository which classifies and stores the electrocardiogram data. The real-time electrocardiogram monitoring system further includes: a broadcasting server which relays the electrocardiogram stored by the monitoring server to a remote place; and a viewer which views the electrocardiogram data received from the broadcasting server.

12 Claims, 10 Drawing Sheets

REAL-TIME ELECTROCARDIOGRAM MONITORING SYSTEM AND METHOD, PATCH-TYPE ELECTROCARDIOGRAPH, TELECOMMUNICATION APPARATUS

TECHNICAL FIELD

The present invention relates to an electrocardiogram monitoring technique, and more particularly to a real-time electrocardiogram monitoring system and method which is capable of acquiring and relaying an electrocardiogram signal of a patient located at a remote place in real time, a patch-type electrocardiograph and a telecommunication apparatus.

BACKGROUND ART

In general, measurement for an electrocardiogram signal is made by an electrocardiogram monitor located in a hospital and a Holter electrocardiograph located out of the hospital. The electrocardiogram monitor located in the hospital employs a method of delivering an electrocardiogram signal to a central monitor located in the hospital via a wired or wireless local area network (LAN) and monitoring the electrocardiogram signal at the central monitor. The Holter electrocardiograph located out of the hospital is an apparatus for measuring an electrocardiogram for a subject who wears an electrocardiograph for 24 or 48 hours or longer, storing an abnormal signal, if it is detected, and analyzing the stored abnormal signal through a computer of the hospital visited by the subject in time.

With recent development of telecommunications technology, there have been developed techniques for transmitting an electrocardiogram signal to a remote place by wireless.

Examples of conventional techniques for transmitting an electrocardiogram signal or a bio-signal to a remote place by wireless include an ambulatory electrocardiograph, which is disclosed in Korean Patent Registration No. 10-0429823, and a real-time bio-signal monitoring system using a wireless communication network, which is disclosed in Korean Patent Registration No. 10-0197580.

The disclosed ambulatory electrocardiograph includes a typical electrocardiogram acquisition means with an abnormal signal decision algorithm contained therein, and interconnects a wireless communication device, a printer and a PCMCIA (Personal Memory Card International Association) and so on. In this electrocardiograph, if an abnormal signal occurs, an electrocardiogram signal is stored for a certain period of time before and after the occurrence of the abnormal signal and is transmitted to a remote hospital via a wireless communication network for a doctor's prescription.

The disclosed real-time bio-signal monitoring system using a wireless communication network checks bio-signal data and transmits an abnormal signal, if any, to a wireless relay station via an internal wireless modem. The wireless relay station transmits the abnormal signal to a bio-signal monitoring server of a hospital, and the bio-signal monitoring server monitors reception signals and transmits a measure and emergency prescription method corresponding to the monitored signal to a bio-signal holder apparatus.

The above conventional techniques relate to transmission of bio-signals to a remote monitoring server via a public wireless communication device incorporated in the electrocardiograph, wherein the bio-signals are consistently and automatically monitored and an abnormal signal is transmitted to a remote place only if it occurs. However, in case of intermittent arrhythmia or myocardial infarction, it has very short duration and its normal signal has substantially the same shape as its abnormal signal, thereby making automatic detection by a machine difficult. Further, it requires a complicated signal processing algorithm for the automatic detection. In addition, since it is common that an electrocardiogram is transmitted to a remote hospital rather than home, there is a need for a mobile device which can be freely moved in various regions such as in vehicles, mountains and so on.

In addition, the portable electrocardiograph need be convenient and simple in its measurement and usage while being compact and lightweight for portability.

However, if the portable electrocardiograph is installed with a complicated signal processing algorithm for real-time monitoring and transmission, it requires a high performance processor, which may result in great increase in system size and power consumption.

In other words, since the size of the portable electrocardiograph has direct relation with portability and power consumption also has direct relation with a battery size, it was very difficult to achieve a portable electrocardiograph for acquisition of electrocardiogram signals.

DISCLOSURE OF INVENTION

Technical Problem

The present invention has been designed to overcome the above and other problems, and it is an object of the invention to provide a real-time electrocardiogram monitoring system and method which is capable of monitoring an electrocardiogram signal for a subject in real time at a remote place while minimizing inconvenience of measurement of the electrocardiogram signal, wherein the system includes a personal measuring system including a compact flexible measuring device which is capable of being attached on a chest of the subject and performing near-field communication and a communication terminal which is capable of performing far-field communication, and a server system which is capable of monitoring an electrocardiogram for the subject based on electrocardiogram measurement information provided by the personal measuring system and relaying or broadcasting the electrocardiogram measurement information, and a patch-type electrocardiograph, and a telecommunication apparatus.

Technical Solution

To achieve the above and other objects, according to an aspect, the present invention provides a real-time electrocardiogram monitoring system including: a patch-type electrocardiograph which is attached to a skin of a subject in the form of a patch, measures an electrocardiogram of the subject, and generates and transmits first electrocardiogram data of a first frame format for near-field transmission of the measured electrocardiogram signal; a relay-type communication device which receives the first electrocardiogram data from the patch-type electrocardiograph, extracts electrocardiogram data, and combines the extracted electrocardiogram with identification information of the subject to generate second electrocardiogram data of a second frame format for far-field transmission; a monitoring server which receives the second electrocardiogram data from the relay-type communication device, extracts the electrocardiogram data and the subject identification information, and classifies, stores and outputs in real time the electrocardiogram data based on the subject identification information; and a repository which classifies and stores the electrocardiogram data.

Preferably, the real-time electrocardiogram monitoring system further includes: a broadcasting server which relays the electrocardiogram stored by the monitoring server to a remote place; and a viewer which views the electrocardiogram data received from the broadcasting server.

Advantageous Effects

The present invention provides a real-time electrocardiogram monitoring system in which a real-time measured electrocardiogram signal is remotely transmitted to a server using a patch-type wireless measuring device and a relay and the server monitors and broadcasts the remotely received electrocardiogram signal, which is suitable and requisite for a health control system using ubiquitous health care.

In addition, the present invention provides a real-time electrocardiogram monitoring system which is wearable with no interference in daily life and is capable of diagnosing and managing conditions of a subject promptly and precisely by monitoring and broadcasting an electrocardiogram signal in real time.

In addition, the present invention provides a real-time electrocardiogram monitoring system which is capable of providing an innovative diagnosis and management method for many persons with heart disease and patients who undergo a heart surgery, which may result in reduction of temporal, economical and social burdens which may be imposed on patients.

BEST MODE FOR CARRYING OUT THE INVENTION

<Electrocardiogram Monitoring System>

Figure 1:
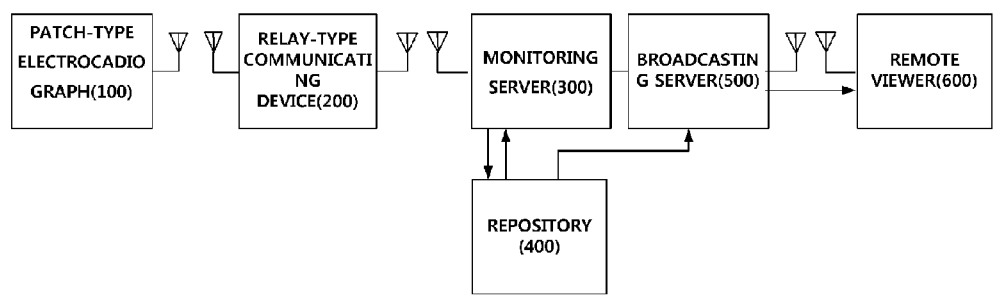
FIG. 1 is a view showing a configuration of a real-time electrocardiogram monitoring system according to a preferred embodiment of the present invention.

A configuration of a real-time electrocardiogram monitoring system according to a preferred embodiment of the present invention will be described below with reference to FIG. 1.

The electrocardiogram monitoring system includes a patch-type electrocardiograph 100 which measures electrocardiogram signals, a relay-type communication device 200 which arranges and relays the electrocardiogram signals from the electrocardiograph 100 to a remote place, a monitoring server 300 which monitors and stores the electrocardiogram signals from the electrocardiograph 100 in real time, a repository 400 having a database in which a list of the stored electrocardiogram signal from the monitoring server 300 and associated data are registered, a broadcasting server 500 which relays the real-time electrocardiogram signals stored in the monitoring server 300 and the electrocardiogram signals registered in the database of the repository to a remote place, and a viewer 600 located at the remote place.

The patch-type electrocardiograph 100 and the relay-type communication device 200 exchange data with a UHF band near-field wireless communication device or a human body communication device. In particular, the patch-type electrocardiograph 100 is made so small and light that it can be worn on a chest and the relay-type communication device 200 also is made so compact that it is easy to carry.

<Patch-Type Electrocardiograph>

The patch-type electrocardiograph 100 generally includes an adhesive pad having three electrodes located on a single plane; an analog signal processor which processes an analog electrocardiogram signal in real time; a digital signal processor which processes the processed analog electrocardiogram signal into first electrocardiogram data of a first frame format which is suitable for digital transmission; and a UHF transmitter which transmits the first electrocardiogram data in a short range.

Figure 2:
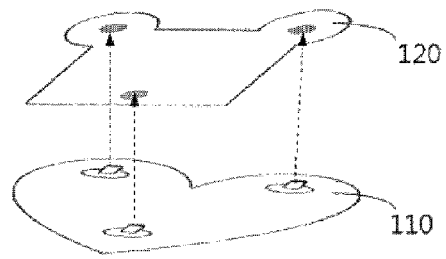
FIG. 2 is a view showing an external structure of a patch-type electrocardiograph according to a preferred embodiment of the present invention.

Here, a structure of the patch-type electrocardiograph 100 will be described with reference to FIG. 2.

The patch-type electrocardiograph 100 includes an adhesive disposable tripolar pad 110 used for electrocardiogram measurement and a reusable electrocardiogram measuring unit 120. The tripolar pad 110 is formed by adhesively placing three electrodes, which are configured by bipolar and unipolar electrodes, on a bare pad. The electrocardiogram measuring unit 120 is formed by a flexible circuit board which can make direct couple to the tripolar pad 110 and does not interfere with the tripolar pad 110.

Figure 3:
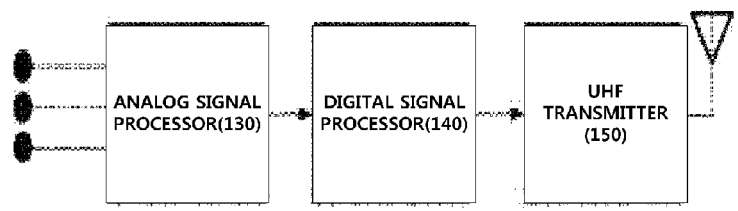
FIG. 3 is a block diagram showing a patch-type electrocardiograph according to a preferred embodiment of the present invention.

The configuration of the electrocardiogram measuring unit 120 will be described in more detail below with reference to FIG. 3.

As mentioned above and shown in the FIG. 3, the electrocardiogram measuring unit 120 includes an analog signal processor (ASP) 130, a digital signal processor (DSP) 140 and a UHF wireless transmitter 150.

Here, the ASP 130 generally includes an implementation amplifier at an initial stage, which receives an electrocardiogram signal from the tripolar pad, a main amplifier which amplifies an output signal from the instrumentation amplifier, a band pass filter which filters power supply noise out of the electrocardiogram signal, a band pass filter which filters respiration noise out of the electrocardiogram signal, a feedback controller which feeds back both of the noises filtered out of the electrocardiogram signal for removal, low pass and high pass filters which filter any signals out of a band electrocardiogram signal, and a buffer amplifier which eliminates distortions of signals by an input of analog-to-digital converter.

Figure 4:
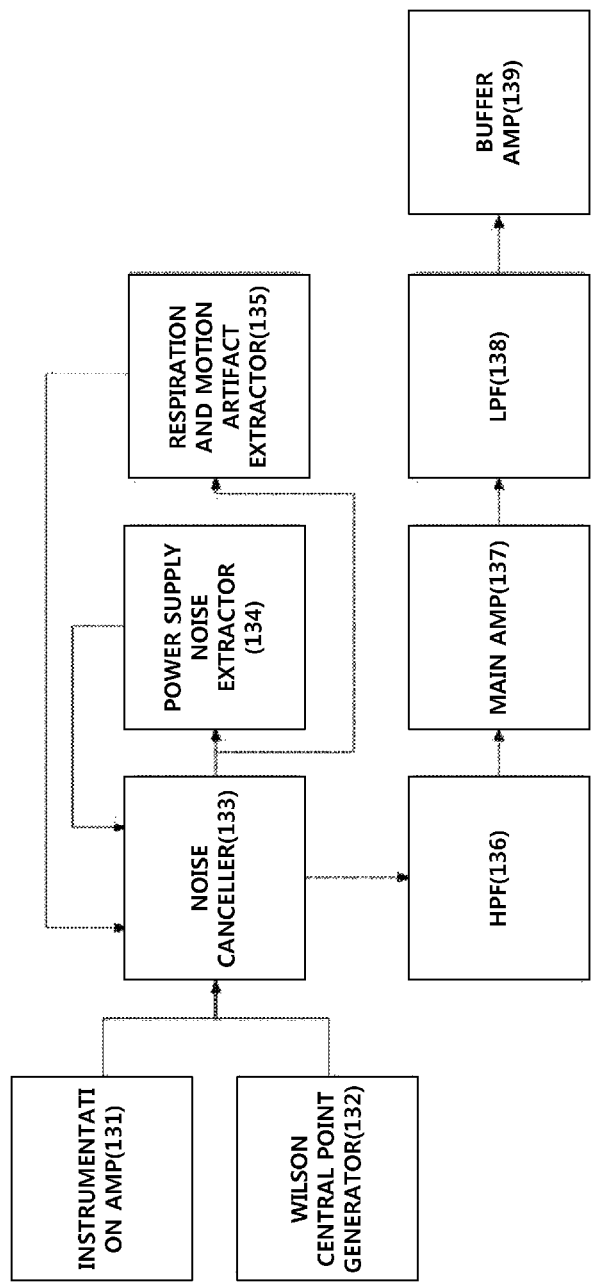
FIG. 4 is a view showing a detailed configuration of an analog signal processor of FIG. 3.

Configuration and operation of the ASP 130 will be described below in detail with reference to FIG. 4.

The ASP 130 of the electrocardiogram measuring unit 120 includes an implementation amplifier 131, a Wilson central point generator 132, a noise canceller 133, a power supply noise extractor 134, a respiration and motion artifact extractor 135, a high pass filter (HPF) 136, a main amplifier 137, a low pass filter (LPF) 138 and a buffer amplifier 139.

The implementation amplifier 131 and the Wilson central point generator 132 convert an electrocardiogram signal of a single channel into a bipolar or unipolar signal which is then input to the noise canceller 133 using a feedback circuit. The noise canceller 133 cancels noise of the electrocardiogram signal through the feedback circuit and provides an electrocardiogram signal with no noise to the power supply noise extractor 134.

The power supply noise extractor 134 extracts only power supply noise through a band pass filter (BPF) of a frequency band corresponding to the power supply noise and the respiration and motion artifact extractor 135 extracts only respiration and motion artifact signals through a BPF of a frequency band corresponding to the respiration and motion artifact. These noise and artifact are cancelled from the original signal by a negative feedback to the noise canceller 133.

The signal with the noise and artifact cancelled may include signals out of a band of the electrocardiogram signal, and thus, the HPF 136 and the LPF 138 are used to eliminate these out-of-band signals and output only a signal having a frequency band between 0.01 and 150 Hz.

When an analog signal is input to the DSP 140 (see FIG. 3), the buffer amplifier 139 serves to eliminate any distortion of a signal due to a load at a stage subsequent to the DSP 140. In one embodiment, an example of the buffer amplifier 139 may include a voltage buffer amplifier.

The DSP 140 converts the electrocardiogram signal received from the ASP 130 into a digital signal. Specifically, such analog-digital conversion is performed with a resolution of 12 bits at a rate of 300 per second, and digital values obtained by the conversion are encoded and delivered to the UHF transmitter 150. Here, the encoding refers to processing of a sum of a 3-bit signal indicating a signal beginning, a 3-bit signal indicating a signal end, and a 10-bit electrocardiogram signal into the total 16-bit (2 bytes) data.

Figure 5:
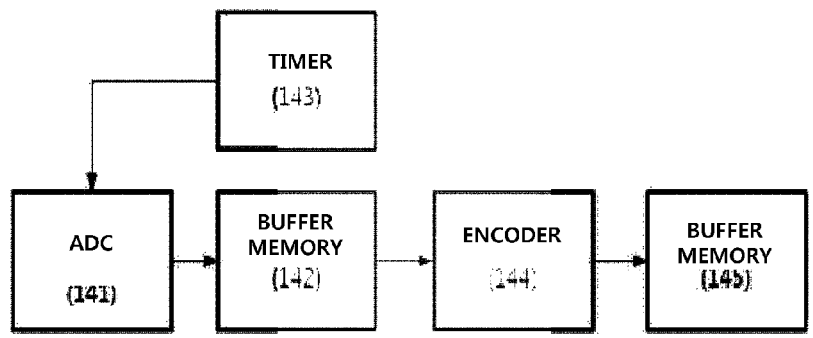
FIG. 5 is a view showing a detailed configuration of a digital signal processor of FIG. 3.
Figure 6:
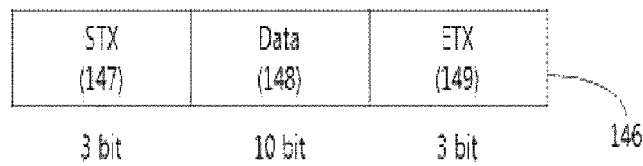
FIG. 6 is a view showing an example configuration of a frame for use in near-field communication according to a preferred embodiment of the present invention.

Configuration and operation of the DSP 140 will be described below with reference to FIGS. 5 and 6. FIG. 5 is a block diagram of the DSP 140, and FIG. 6 illustrates a digital signal frame for wireless transmission.

The DSP 140 includes an analog-to-digital converter (ADC) 141, a 1/300 second timer 143 which is used to control a timing of the ADC 141, a buffer memory 142 which temporarily stores signals output from the ADC 141, an encoder 144 which inserts the signal beginning and end to generate a standard frame, and a buffer memory 145 which is used to output encoded signals in series.

A digital signal frame 146 output from the DSP 140 includes a 3-bit beginning signal 147, a 3-bit ending signal 149 and a 10-bit electrocardiogram signal 148. The beginning and ending signals 147 and 149 allow a decoder in a receiver (see 220 in FIG. 7) to extract correct electrocardiogram data.

The UHF transmitter 150 transmits the electrocardiogram data, i.e., the encoded 16-bit (2 bytes) signal, output from the DSP 140 to a UHF (Ultra High Frequency) domain. In this case, a signal intensity of a transmitting signal makes reference to regulations of any of FCC (Federal Communications Commission), IEEE (Institute of Electrical and Electronics Engineers), ICNIRP (International Commission for Non-Ionizing Radiation Protection), CRMO (Central Radio Management Office) of Korea, etc., and particularly, the transmitting signal is transmitted with power of less than about 1 mW which is a UHF band limit specified by the regulations of ICNIRP which is the strictest regulations, among other things.

<Relay-Type Communication Device>

The relay-type communication device 200 generally includes a UHF band receiver which receives near-field wireless signals or human body communication signals transmitted from the patch-type electrocardiograph 100; a control processor which combines and encodes the received signals and other medical information; and a transceiver which accesses a mobile network or a mobile Internet for long-distance wireless transmission.

In particular, the UHF band receiver of the relay-type communication device 200 includes an antenna, a UHF receiver and a decoder, and the antenna may be a compact UHF band omnidirectional antenna which receives low power transmitting signals. For the purpose of achieving high reception sensitivity for the UHF receiver, it is preferable to use a receiver employing a frequency filter based on a crystal oscillator and a surface acoustic wave (SAW) filter.

The decoder eliminates a separation signal for separating data beginning and end from the received signals and extracts only digitalized electrocardiogram data.

The control processor of the relay-type communication device constructs a transmission frame including information requiring standards for bio-signal transmission, such as an electrocardiogram signal value received from the decoder of the UHF receiver, a patient ID, a kind of the electrocardiogram signal, a sampling rate, etc. The transmission frame is preferably constructed by selecting MFER (Medical waveform Format Encoding Rule), ISO regulations, etc. In addition, the control processor is required to have an input unit for selection of patient-related information and transmission-related rules to be used for construction of signal frames meeting any medical information transmission standard requirements. The input unit of the control processor preferably uses input key buttons or a serial communication device which can input information in association with a personal computer (PC).

In addition, the transceiver for long-distance wireless transmission of the relay-type communication device preferably uses a wireless transceiver which can be connected to a mobile network or a mobile Internet which is in current wide use.

Figure 7:
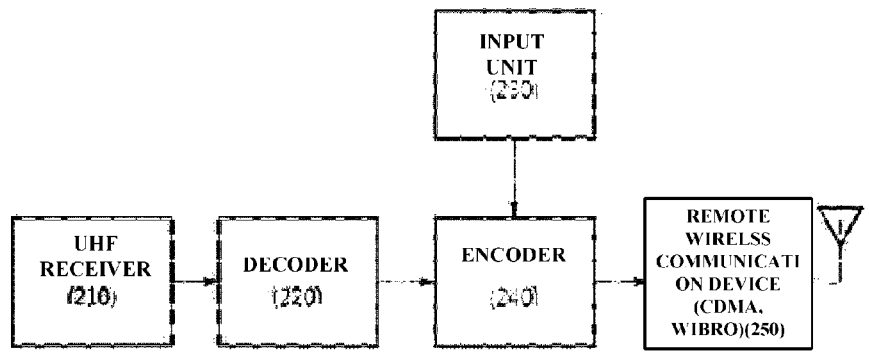
FIG. 7 is a block diagram showing a communication apparatus according to a preferred embodiment of the present invention.

Configuration and operation of the relay-type communication device 200 will be described in detail below with reference to FIG. 7.

The relay-type communication device 200 includes a UHF receiver 210, a decoder 220 which extracts only electrocardiogram data from a received signal, an input unit 230 which receives patient information and various kinds of related information, an encoding unit 240 which generates a frame matching MFER or ISO standards based on the received information and the extracted electrocardiogram data, and a remote wireless communication device 250 such as a CDMA mobile communication device, a mobile Internet communication device or the like for telecommunication.

Figure 8:
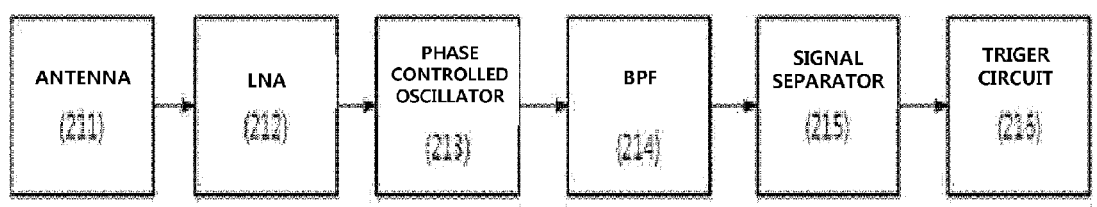
FIG. 8 is a view showing a detailed configuration of a UHF receiver of FIG. 7.

Configuration of the UHF receiver 210 of the relay-type communication device 200 will be described below with reference to FIG. 8.

The UHF receiver 210 includes a reception antenna 211, a low noise amplifier (LNA) 212, a phase controlled oscillator 213 based on a crystal oscillator having high frequency precision, a band pass filter (BPF) 214 which uses a surface acoustic wave (SAW) filter for canceling noise and filtering out only a desired reception signal, a signal separator 215 which separates bits of the filtered signal, and a trigger circuit 216 which represents the separated bit signals as digital signals.

Figure 9:
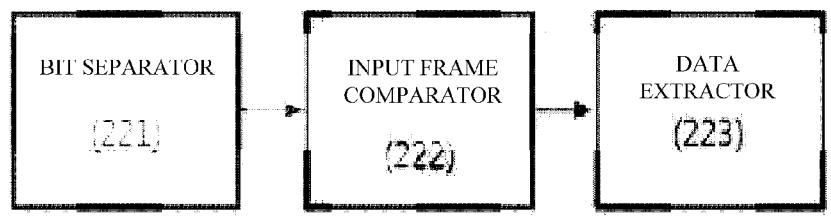
FIG. 9 is a view showing a detailed configuration of a decoder of FIG. 7.

Configuration of the decoder 220 of the relay-type communication device 200 will be described in more detail below with reference to FIG. 9.

The decoder 220 includes a bit separator 221 which separates data for each bit through sampling, a frame comparator 222 which finds beginning bits 147 and ending bits 149 (see FIG. 6) of the received signal and checks whether or not the 10-bit electrocardiogram signal (see FIG. 6) is input based on the found beginning and ending bits, and a data extractor 223 which extracts the electrocardiogram data if the frame is properly input.

Figure 10:
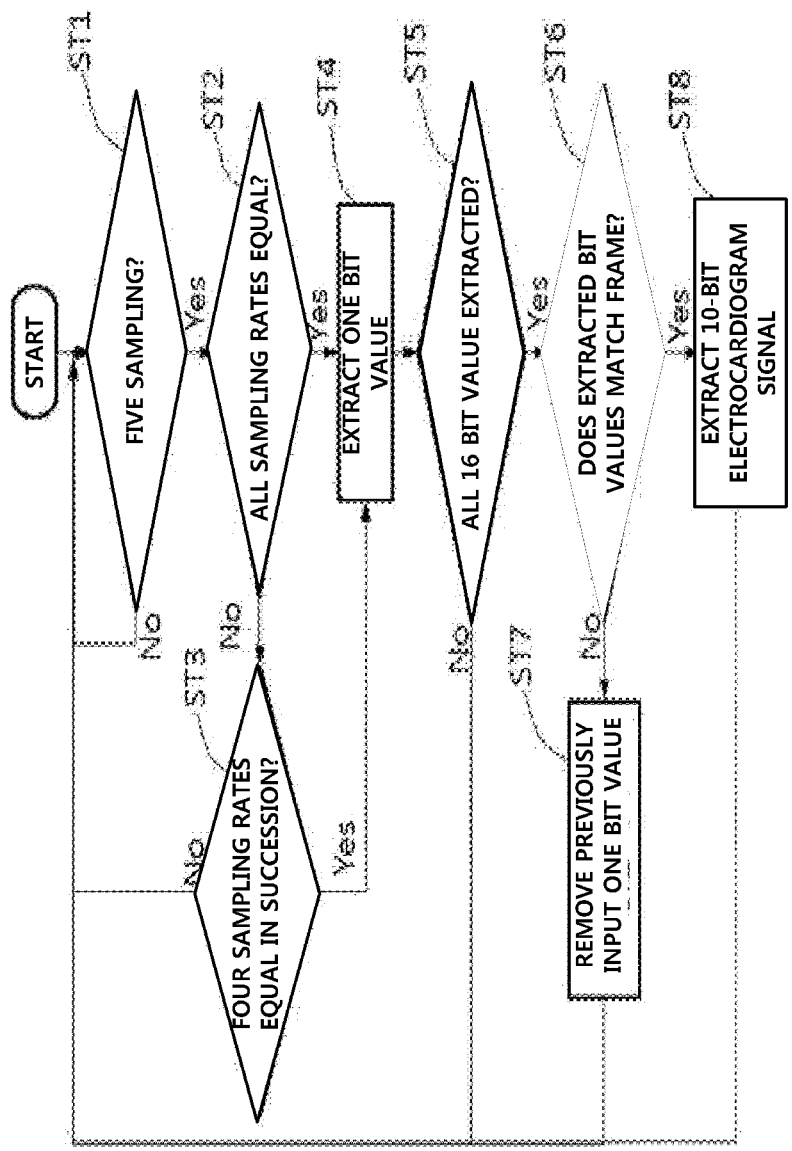
FIG. 10 is a flow chart of the decoder of FIG. 7.

A control method of the decoder 220 of the relay-type communication device 200 will be described below with reference to FIG. 10.

The control method includes a first step (ST1) of determining whether or not five samplings are made by the bit separator 221 of the decoder 220, a second step (ST2) of determining whether or not all five sampling rates are equal if it is determined in ST1 that the five samplings are made, and a third step (ST3) of determining whether or not four consecutive sampling rates are equal if it is determined in ST2 that the five sampling rates are not equal.

Then, the bit separator 221 performs a fourth step (ST4) of extracting and storing one bit value if conditions on the determination in ST2 or ST3 are satisfied.

The frame comparator 222 performs a fifth step (ST5) of determining how many times are ST4 performed, and if it is determined in ST5 that ST4 is performed sixteen times, performs a sixth step (ST5) of comparing a stored 16-bit signal to a predetermined frame.

As a result of the performance of ST6 for frame comparison, if the beginning bits 147, the 10-bit electrocardiogram data 148 and the ending bits 149 are input in accordance with the predetermined frame, the data extractor 223 performs an eighth step (ST8) of extracting the 10-bit electrocardiogram data.

On the other hand, if the beginning bits 147, the 10-bit electrocardiogram data 148 and the ending bits 149 are not equal to the predetermined frame, the frame comparator 222 performs a seventh step (ST7) of removing the first input bit and taking in one more bit and performs an eighth step (ST8) of reducing a data error rate only if the beginning bits 147, the 10-bit electrocardiogram data 148 and the ending bits 149 defined in ST7 are input.

Configuration and external appearance of the input unit 230 and the encoding unit 240 of the relay-type communication device 200 will be described below with reference to FIGS. 11 and 12.

Figure 11:
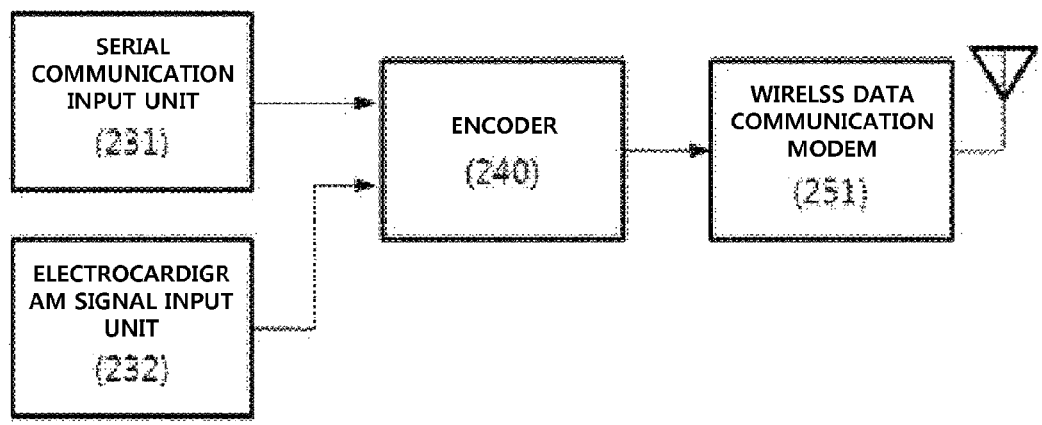
FIG. 11 is a view showing an example configuration of an encoder, an input unit and a remote wireless communication device.
Figure 12:
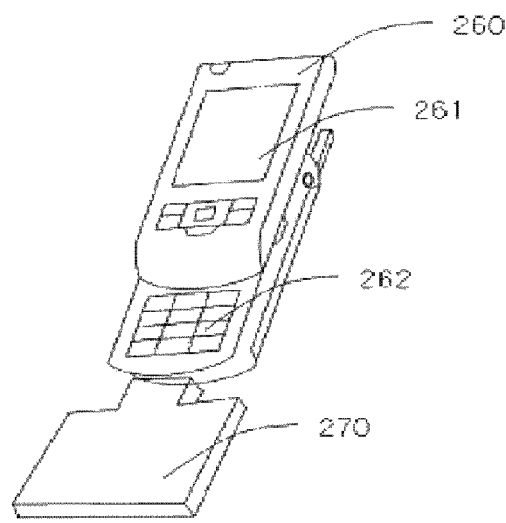
FIG. 12 is a view showing an example application of a relay-type communication device of FIG. 7 to a mobile terminal.

FIG. 11 is a block diagram of the input unit 230 and the encoding unit 240 and FIG. 12 is a view showing an external appearance of the relay-type communication device applied to a mobile terminal.

The input unit 230 and the encoding unit 240 include a serial communication input unit 231 which directly receives serial communication signals, an electrocardiogram signal input unit 232, an encoder 240 and a wireless data communication modem 251 for long-distance communication.

As shown in FIG. 12, the relay-type communication device 200 may be employed for a common mobile terminal 260 to which a dongle 270 may be attached. When the relay-type communication device 200 of the present invention is applied to such a common mobile terminal 260, patient information, measurement information of the electrocardiograph and other related information may be input through a screen 261 and input keys 262 of the mobile terminal 260.

Here, the attachable dongle 270 includes the UHF receiver 210 and the decoder 220 of the relay-type communication device 220 and the mobile terminal 260 incorporates the input unit 230, the encoding unit 240 and the remote wireless communication device 250.

The remote wireless communication device 250 in the relay-type communication device 200 may be applied with mobile phones and wireless modems employing CDMA, WCDMA and HSDPA systems as well as wireless Internet modems of Wibro or and like for use in mobile Internet.

Figure 13:
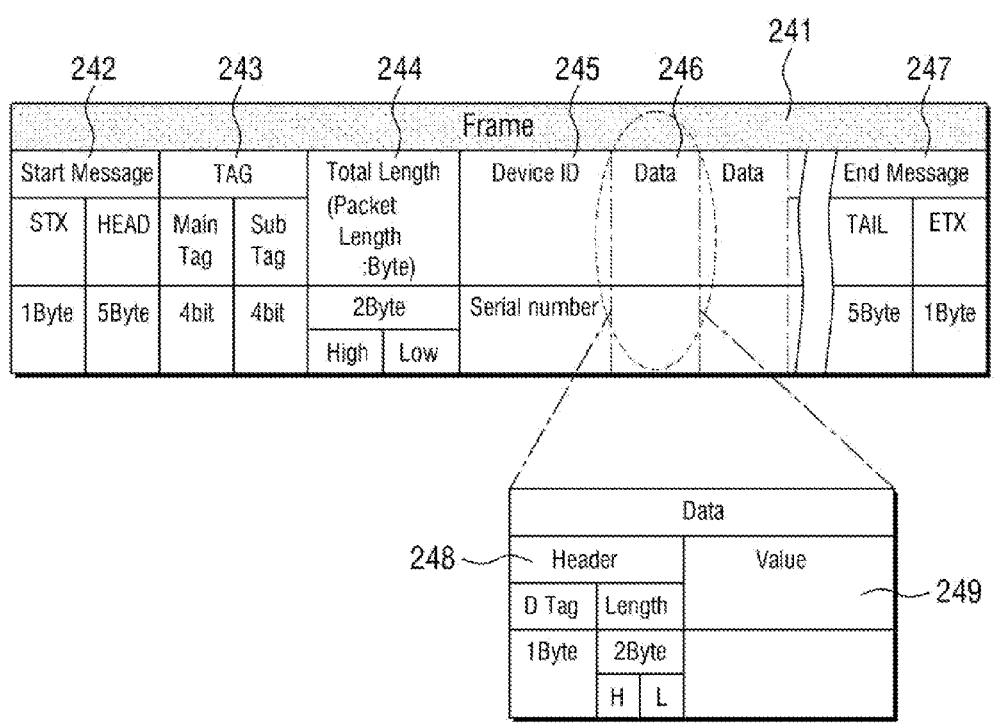
FIG. 13 is a view showing an example configuration of a frame for use in far-field communication according to a preferred embodiment of the present invention.

Referring to FIG. 13 showing signal transmission regulations in the relay-type communication device 200 according to an embodiment of the present invention, an entire signal transmission frame 241 includes a beginning message 242, a tag 243, a length of entire data 244, a device ID 245, electrocardiogram data 246 and an ending message 247. The electrocardiogram data 246 includes a tag indicating the kind of data, a header 248 including data length, and actual electrocardiogram signal values 249. Signals having the frame as configured above can be transmitted in accordance with different national standards including MFER, ISO standards, etc.

<Monitoring Server>

The monitoring server 300 (see FIG. 1) according to a preferred embodiment of the present invention will be described below.

The monitoring server 300 generally includes real-time display software used for real-time display of electrocardiogram data sent from a remote place, a storage for storing electrocardiogram signals separated for each patient and each time, and review software for allowing the stored electrocardiogram signals to be called and reviewed.

In particular, the display software of the monitoring server 300 displays electrocardiogram signals for different patients, which are transmitted in real time, simultaneously on a single screen and displays abnormal signals, for example, abnormal heart rates or other abnormal signals, if found, in the form of a pop-up on the same screen.

To this end, the display software incorporates a function of detecting R peaks f a received electrocardiogram signal and calculating an interval between the R peaks, and measuring a heart rate per minute, and an algorithm for indicating abnormal signals if the heart rate is more or less than a predetermined rate.

In addition, a repository of the monitoring server 300 separates electrocardiogram signals transmitted in real time for each patient ID and stores the separated electrocardiogram signals in its own database while automatically preparing a list of storage for each patient ID.

In addition, a review function of the monitoring server 300 allows a user to select and view an electrocardiogram signal for each patient and each time from the prepared list of storage.

Figure 14:
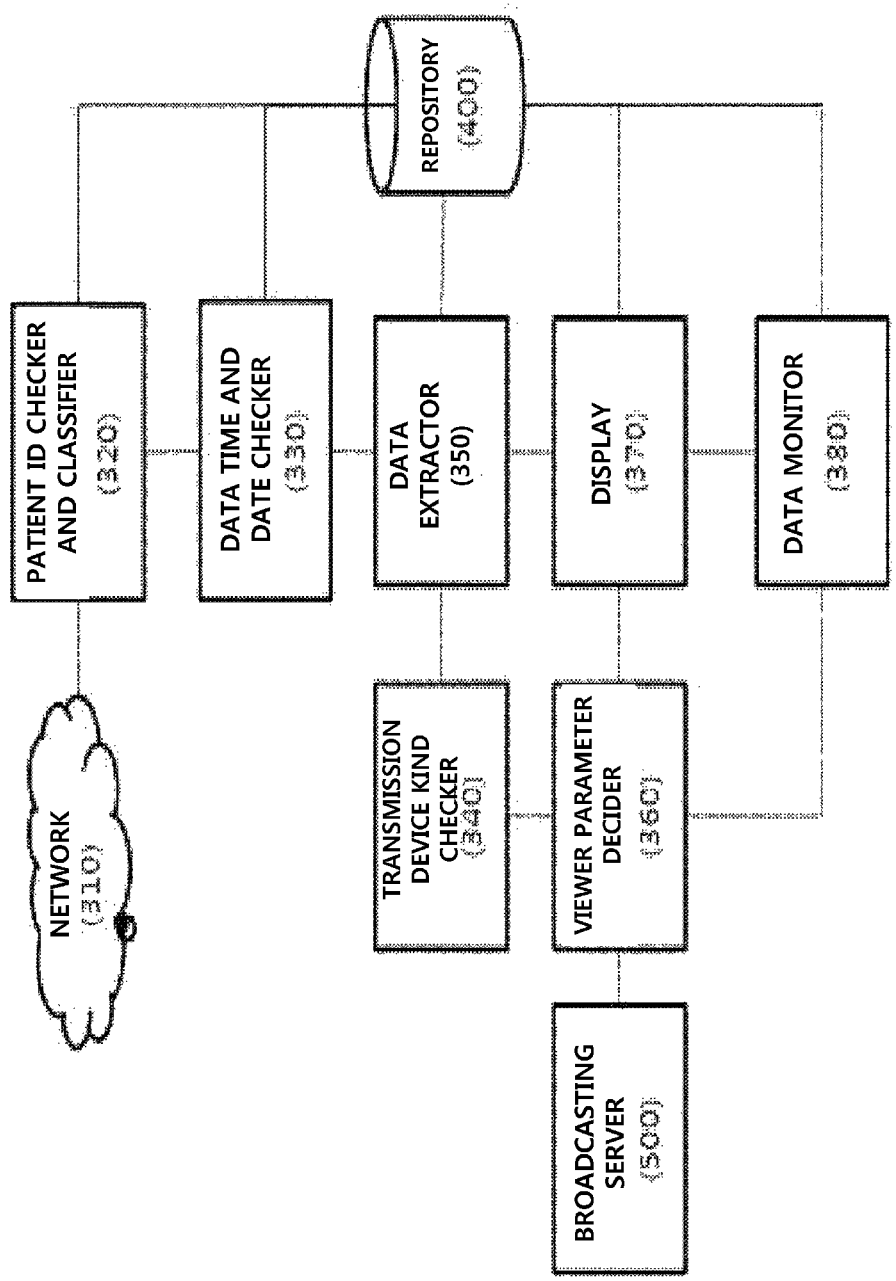
FIG. 14 is a view showing a configuration of a monitoring server according to a preferred embodiment of the present invention.

Configuration of the monitoring server 300 according to a preferable embodiment of the present invention will be described below with reference to FIG. 14.

The monitoring server 300 includes a patient ID checker and classifier 320 connected to a network 310, a data time and date checker 330, a transmission kind checker 340, a data extractor 350 for database storage, a viewer parameter decider 360 for display, a display 370 which displays real-time electrocardiogram signals for different patients on a monitor, and a data monitor 380 which monitors the electrocardiogram signals in real time and generates a warning.

In addition, the monitoring server 300 may include some or all of the function of storing extracted data in the repository 400 and delivering the data to a broadcasting server 500.

The patient ID checker and classifier 320 of the monitoring server 300 checks patient IDs transmitted when a transmission device accesses the server 300 via a network, and converts the checked patient IDs into unique IDs in the server 300.

In general, patient IDs use patient numbers or patient names. However, if there are different patients having the same name, IDs of the different patients may be identified as the same patient. Accordingly, in this embodiment, new patient IDs using a combination of patient's name, age, number and so on in the database are generated and managed at the time of device access. Generation time and date of data acquired with their own IDs classified by the patient ID checker and classifier 320 are checked by the data time and data checker 330. Since the network 310 may have some problems of message delivery delay, overlapping delivery, etc., time values in the data frame 241 (see FIG. 13) are used to determine time of data generation and the presence of overlapping data, and the kind of data is detected based on the determined tome of data generation. Since transmission data have different sampling frequencies and different analog-to-digital conversion coefficients for each device, the transmission data are checked by the transmission device kind checker 340 referring to values of the data frame 241.

The checked transmission data are delivered to the viewer parameter decider 360 for adjusting time interval and size at the time of display, the data extractor 350 and the broadcasting server 500.

The data extractor 350 separates data for each table from the delivered data frame 241 in accordance with a database structure and stores the separated data in the database of the repository 400.

The viewer parameter decider 360 checks a size of the entire window being displayed and the number of patients, decides a data display size, a data display interval, etc. in accordance with the checked window size and the number of patients, and transmits the decided data display size and display interval to the display 370 and the data monitor 380.

The display 370 displays signal values using parameter values decided in the viewer parameter decider 360 and calls the data stored in the repository 400 to its review screen depending on an input from a user.

The data monitor 380 serves to monitor the data input and displayed in real time and inform the display 370 of an emergency situation using a pop-up if the data are out of a predetermined range of values. In addition, the data monitor 380 may store time and date at which the emergency situation occurs and a relevant patient's ID in the repository 400 and confirm them in detail whenever necessary.

<Repository>

Figure 15:
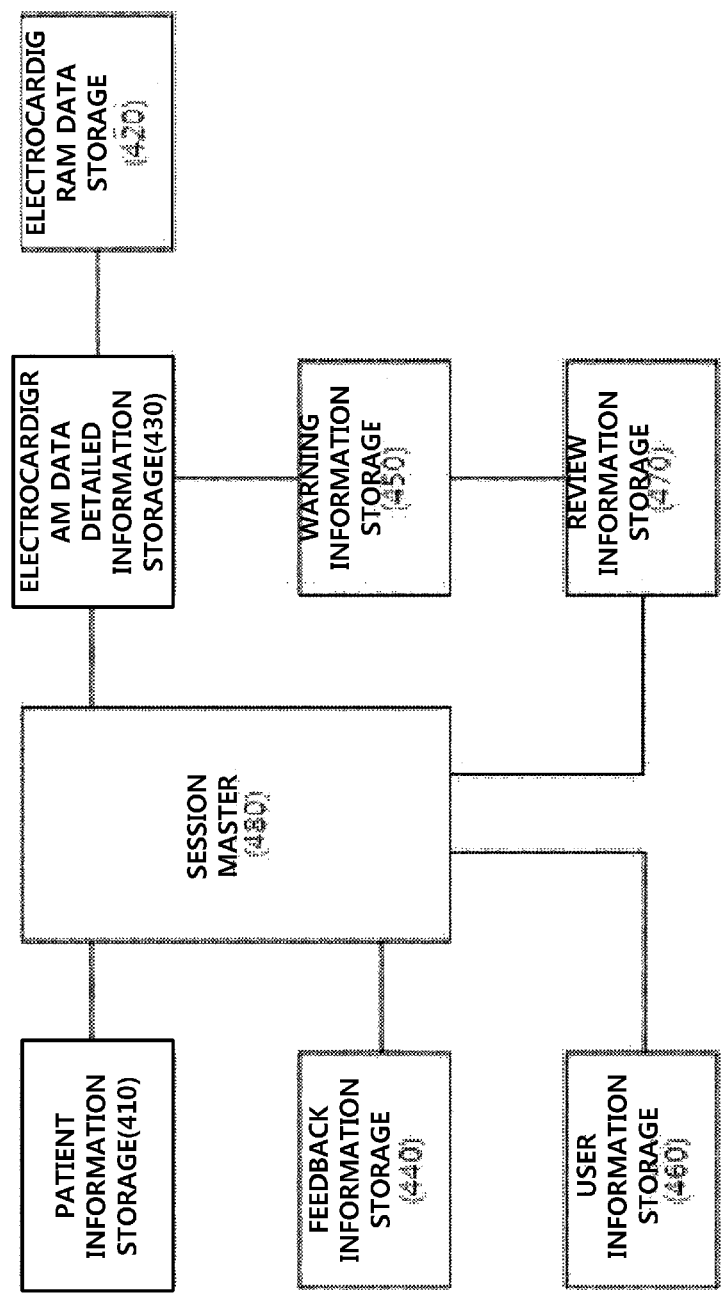
FIG. 15 is a view showing a structure of a repository according to a preferred embodiment of the present invention.

Configuration of the repository 400 according to an embodiment of the present invention will be described below with reference to FIG. 15.

The repository 400 includes a patient information storage 410, an electrocardiogram data storage 420, an electrocardiogram data detailed information storage 430, a feedback information storage 440, a warning information storage 450, a user information storage 460, a review information storage 470 and a session master 480.

The repository 400 receives electrocardiogram data from the monitoring server 300 and stores patient IDs, date and time of data generation, the electrocardiogram data, format information for display, and additional bio-information which is generated by a separate algorithm.

Figure 16:
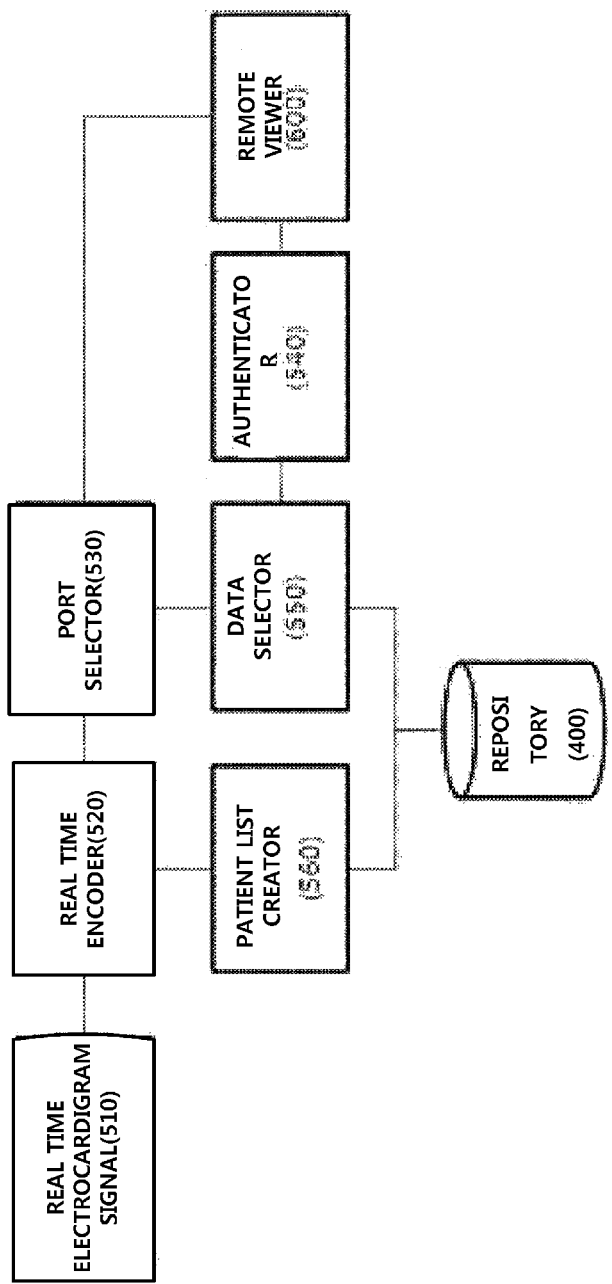
FIG. 16 is a view showing a configuration of a broadcasting server according to a preferred embodiment of the present invention.

In addition, if there is a request for reading of the stored information from a remote viewer, the repository 400 provides a port selector 530 of a broadcasting server 500 (see FIG. 16) with the requested information, which is then transmitted to a remote viewer 600 (see FIG. 16).

The patient information storage 410 of the repository 400 includes basic patients' personal information such as patients' posts, names, IDs, hospital rooms and wards, sexes, addresses, ages, contacts and so on.

The electrocardiogram data storage 420 of the repository 400 stores the electrocardiogram data converted into a particular format in a digital format which can be easily converted into a required different format at an external request.

The feedback information storage 440 of the repository 400 stores information on reading results attached with users' IDs and diagnosis-related information such as doctors' diagnosis opinions and the like.

The warning information storage 450 of the repository 400 stores information corresponding to a upper limit, a lower limit, a warning code, warning time, a warning value and so on for various parameters of the electrocardiogram signal if a warning signal against an abnormal signal is generated while the electrocardiogram signal is being monitored.

The user information storage 460 of the repository 400 stores user access information including user IDs, access dates and times and so on of system users including a remote user who requests a review.

The review information storage 470 of the repository 400 stores information on recent access date and times if the broadcasting server 500 is accessed in order to review the data stored in the repository 400 at a remote place.

The session master 480 of the repository 400 temporarily stores link information for data retrieval and search between the storages of the repository 400.

<Broadcasting Server>

The broadcasting server 500 relays electrocardiogram data for each patient in real time to remote users who access the server 500 through an authentication process and provides a function of reviewing stored data in addition to the real-time relay function.

More specifically, the broadcasting server 500 allows the remote users to check real-time electrocardiograms of individual patients in real time and also waveforms of electrocardiograms which have been already stored in the repository of the monitoring server. Since the remote users need to be able to monitor an electrocardiogram of the same patient by accessing the broadcasting server simultaneously via the Internet, a mobile Internet or a mobile telephone network using their own PDAs or PCs, the broadcasting server 500 assigns the remote accessors with their respective ports to allow them to read data simultaneously.

A structure of the broadcasting server 500 according to a preferable embodiment of the present invention will be described below with reference to FIG. 16.

The broadcasting server 500 includes a real-time encoder 520 which receives a real-time electrocardiogram signal 510 and encodes it in real time, a port selector 530 which delivers real-time encoded data for each patient ID to respective communication ports, an authenticator 540 which authenticates an access of a remote viewer 600, and a data selector 550 which transmits data requested by the authenticated remote viewer 600 to the remote viewer 600 again.

The real-time encoder 520 of the broadcasting server 500 performs a real-time encoding process to allow an electrocardiogram signal for each patient delivered from the monitoring server 300 to be transmitted to the remote viewer. The real-time encoded data for each patient are relayed to a corresponding port in the port selector 530. The port selector 530 relays a real-time signal according to an instruction from the data selector 550 in order to detect the kind of a signal requested by the remote viewer 600. In addition, if a signal stored in addition to the real-time signal is input to the data selector 550, the data selector 550 also relays the input signal to the remote viewer 600.

If the remote viewer 600 requests for data on a desired patient or patients through an authentication process by the authenticator 540, the data selector 550 of the broadcasting server 500 issues a port connection instruction to the port selector 530 to allow the real-time encoded signal to be transmitted to a corresponding port. In addition, if the remote viewer 600 requests a patient's medical history from a patient list, the data selector 550 calls a stored signal from the repository 400 and inputs it to the port selector 530, which is then transmitted to the remote viewer 600.

The remote viewer 600 accesses the broadcasting server 500 via a wired or wireless network and is authenticated by the authenticator 540. According to this authentication, the viewer is vested with an accessible range of information and receives an accessible patient list from a patient list creator 560. The remote viewer 600 may include any computer on a network or a portable communication device such as a PDA or a mobile phone in addition to the monitoring server.

If a signal for a new patient among the real-time encoded signals is input to the patient list creator 560, the patient list creator 560 updates an ID of the patient and deletes the patient ID from the patient list if the patient ID is deleted from the repository.

INDUSTRIAL APPLICABILITY

The present invention can be applied to a wearable or portable health control system which employs a patch-type wireless measuring device and a relay. Thus, the present invention can make great contributions to development of ubiquitous health care industries in which IT technologies are utilized for medical industries.

Although a few exemplary embodiments have been shown and described, it will be appreciated by those skilled in the art that adaptations and changes may be made in these exemplary embodiments without departing from the spirit and scope of the invention, the scope of which is defined in the appended claims and their equivalents.

The invention claimed is:

1. A real-time electrocardiogram monitoring system comprising:
   a patch-type electrocardiograph which is attached to a skin of a subject in the form of a patch-type form, configured to measure an electrocardiogram of the subject, and to generate and transmit first electrocardiogram data of a first frame format for near-field transmission of the measured electrocardiogram signal;
   a relay-type communication device configured to receive the first electrocardiogram data from the patch-type electrocardiograph, to extract electrocardiogram data, and combine the extracted electrocardiogram with identification information of the subject to generate second electrocardiogram data of a second frame format for far-field transmission;
   a monitoring server configured to receive the second electrocardiogram data from the relay-type communication device, to extract the electrocardiogram data and the subject identification information of the subject, to classify, to store and to output in real time the electrocardiogram data based on the subject identification information of the subject; and
   a repository configured to classify and store the electrocardiogram data, wherein in response to receipt of requests by viewers of the electrocardiogram data, an authenticator is configured to perform a multilevel authentication to determine accessible class of the electrocardiogram data, the multilevel authentication specifying a different accessible class of viewer which is classified based on each of the viewers and a data selector that is configured to transmit only the electrocardiogram data upon detection of a successful authentication corresponding to each level of the multilevel authentication based on each of the viewers.

2. The real-time electrocardiogram monitoring system of claim 1, further comprising:
   a broadcasting server configured to relay the electrocardiogram stored by the monitoring server to a remote place; and to display the electrocardiogram data received from the broadcasting server.

3. The real-time electrocardiogram monitoring system of claim 1, wherein the patch-type electrocardiograph comprises:
   an adhesive pad having three electrodes located on a single plane;
   an analog signal processor configured to perform amplification and noise cancellation of the electrocardiogram signal input to the three electrodes;
   a digital signal processor configured to convert an analog signal output from the analog signal processor into a digital signal and to process the electrocardiogram data into the first electrocardiogram data of the first frame format for near-field transmission; and
   a UHF band transmitter configured to transfer the first electrocardiogram data in the near-field.

4. The real-time electrocardiogram monitoring system of claim 3, wherein the analog signal processor comprises:
   an amplifier configured to receive and to amplify the electrocardiogram signal from the adhesive pad;
   a band pass filter configured to separate a signal of power supply noise and a signal of respiration noise from the amplified electrocardiogram signal;
   a noise canceller configured to receive the electrocardiogram signal and the signal of power supply noise and the signal of respiration noise and to cancel the signal of power supply noise and the signal of respiration noise from the electrocardiogram signal; and
   a filter configured to eliminate signals out of a band of the electrocardiogram signal.

5. The real-time electrocardiogram monitoring system of claim 3, wherein the digital signal processor comprises:
   an analog-to-digital converter configured to convert the electrocardiogram signal received from the analog signal processor into the electrocardiogram data; and an encoder configured to generate the first electrocardiogram data of the first frame format by adding data indicating a beginning and an end to the electrocardiogram data.

6. The real-time electrocardiogram monitoring system of claim 1, wherein the relay-type communication device comprises:
- a UHF band receiver configured to receive the first electrocardiogram data from the patch-type electrocardiograph;
- a decoder configured to extract electrocardiogram data from the first electrocardiogram data;
- a user interface to receive user input;
- a transceiver configured to perform communication with the monitoring server located at a remote place; and
- an encoder configured to generate the second electrocardiogram data of the second frame format by combining the electrocardiogram data and the subject identification information comprising one or more of subject information, device information and medical information through the user interface, and
- to transmit the second electrocardiogram data to the monitoring server through the transceiver.

7. The real-time electrocardiogram monitoring system of claim 6, wherein the UHF band receiver comprises:
- an omnidirectional UHF band antenna; a low noise amplifier which amplifies a signal received through an omnidirectional band antenna; and
- a surface acoustic wave filter configured to filter the amplified signal.

8. The real-time electrocardiogram monitoring system of claim 6, wherein the decoder comprises:
- a bit separator configured to separate data for each string of bits from a received signal;
- a frame comparator configured to compare a string of beginning bits, ending bits and electrocardiogram data bits from the data for each string of bits to a predetermined frame; and a data extractor which extracts the electrocardiogram data if the string of bits matches the predetermined frame.

9. The real-time electrocardiogram monitoring system of claim 6, wherein the encoder is configured to generate the second electrocardiogram data of the second frame format including the subject identification information input from the user interface and electrocardiogram data, a beginning message and an ending message input from the decoder.

10. The real-time electrocardiogram monitoring system of claim 1, wherein the monitoring server comprises:
- real-time display software configured to display the electrocardiogram data extracted from the second electrocardiogram data;
- storage software configured to classify and to store the electrocardiogram data extracted from the second electrocardiogram data for each subject and each time; and
- review software configured to output the stored electrocardiogram data.

11. The real-time electrocardiogram monitoring system of claim 10, wherein the storage software of the monitoring server comprises:
- a patient checker and classifier configured to extract the identification information of the subject included in the second electrocardiogram data and to convert the identification information of the subject into unique identification information;
- a data time and date checker configured to check data generation time and overlapping reception using time information included in the second electrocardiogram data; and
- a data extractor configured to classify the second electrocardiogram data based on the unique identification information and the data generation time.

12. The real-time electrocardiogram monitoring system of claim 10, wherein the display software comprises:
- a viewer parameter decider which decides display size and interval of the electrocardiogram data to be displayed based on a size of an entire window and the number of subjects;
- a display controller configured to output the electrocardiogram data to a display based on the display size and interval of the electrocardiogram data decided in the viewer parameter decider; and
- a data monitor configured to monitor the electrocardiogram data outputted in the display controller and to display electrocardiogram data, which are out of a prescribed range, on the display controller in a form of a pop-up.

* * * * *